US006528464B1

(12) United States Patent
Xia et al.

(10) Patent No.: US 6,528,464 B1
(45) Date of Patent: Mar. 4, 2003

(54) COMPOSITION AND METHOD FOR INHIBITING UPTAKE OF BIGUANIDE ANTIMICROBIALS BY HYDROGELS

(75) Inventors: Erning Xia, Penfield, NY (US); Richard V. Smerbeck, Pittsford, NY (US); Rebecca Franklin, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/932,356

(22) Filed: Aug. 17, 2001

(51) Int. Cl.$^7$ ................................. C11D 3/48
(52) U.S. Cl. ...................... 510/112; 510/113; 510/114; 510/382; 514/839; 514/840
(58) Field of Search ................. 514/839, 840; 510/112, 113, 114, 382

(56) References Cited

U.S. PATENT DOCUMENTS

| | | | |
|---|---|---|---|
| 4,136,250 A | 1/1979 | Mueller et al. ............... 528/29 |
| 4,153,641 A | 5/1979 | Deichert et al. ............ 260/827 |
| 4,463,149 A | 7/1984 | Ellis ........................... 526/279 |
| 4,604,479 A | 8/1986 | Ellis ........................... 556/440 |
| 4,686,267 A | 8/1987 | Ellis et al. .................. 526/245 |
| 4,740,533 A | 4/1988 | Su et al. ..................... 523/106 |
| 4,758,595 A | 7/1988 | Ogunbiyi et al. ........... 514/635 |
| 4,826,936 A | 5/1989 | Ellis ........................... 526/258 |
| 4,996,275 A | 2/1991 | Ellis et al. .................. 526/245 |
| 5,006,622 A | 4/1991 | Kunzler et al. ............. 526/309 |
| 5,032,658 A | 7/1991 | Baron et al. ................ 526/321 |
| 5,034,461 A | 7/1991 | Lai et al. .................... 525/100 |
| 5,070,215 A | 12/1991 | Bambury et al. ........... 556/418 |
| 5,177,165 A | 1/1993 | Valint, Jr. et al. .......... 526/245 |
| 5,177,168 A | 1/1993 | Baron et al. ................ 526/321 |
| 5,219,965 A | 6/1993 | Valint, Jr. et al. .......... 526/245 |
| 5,236,969 A | 8/1993 | Kunzler et al. ............. 523/108 |
| 5,260,000 A | 11/1993 | Nandu et al. ................ 264/2.1 |
| 5,270,418 A | 12/1993 | Kunzler et al. ............. 526/309 |
| 5,298,533 A | 3/1994 | Nandu et al. ............... 523/106 |
| 5,310,779 A | 5/1994 | Lai ............................. 524/588 |
| 5,321,108 A | 6/1994 | Kunzler et al. ............. 526/242 |
| 5,336,797 A | 8/1994 | McGee et al. .............. 556/419 |
| 5,346,976 A | 9/1994 | Ellis et al. .................. 526/279 |
| 5,358,995 A | 10/1994 | Lai et al. .................... 524/547 |
| 5,364,637 A | 11/1994 | Deet et al. .................. 424/464 |
| 5,364,918 A | 11/1994 | Valint, Jr. et al. .......... 526/245 |
| 5,387,662 A | 2/1995 | Kunzler et al. ............. 526/245 |
| 5,449,729 A | 9/1995 | Lai ............................. 526/286 |
| 5,512,205 A | 4/1996 | Lai ....................... 252/182.14 |
| 5,539,016 A | 7/1996 | Kunzler et al. ............. 523/107 |
| 5,610,204 A | 3/1997 | Lai ............................. 522/44 |
| 5,610,252 A | 3/1997 | Bambury et al. ........... 526/279 |
| 5,616,757 A | 4/1997 | Bambury et al. ........... 556/419 |
| 5,639,908 A | 6/1997 | Lai ............................. 560/158 |
| 5,648,515 A | 7/1997 | Lai ............................. 560/115 |
| 5,708,094 A | 1/1998 | Lai et al. .................... 525/296 |
| 5,710,302 A | 1/1998 | Kunzler et al. ............. 556/434 |
| 5,714,557 A | 2/1998 | Kunzler et al. ............. 526/279 |
| 5,726,733 A | 3/1998 | Lai et al. .................... 351/160 |
| 5,824,719 A | 10/1998 | Kunzler et al. ............. 523/106 |
| 5,858,937 A | 1/1999 | Richard et al. ............. 510/112 |
| 5,908,906 A | 6/1999 | Kunzler et al. ............. 526/279 |
| 5,914,355 A | 6/1999 | Kunzler ...................... 523/106 |
| 5,945,465 A | 8/1999 | Ozark et al. ................ 523/106 |
| 5,969,076 A | 10/1999 | Lai et al. .................... 528/28 |
| 5,981,669 A | 11/1999 | Valint, Jr. et al. .......... 525/477 |
| 5,981,675 A | 11/1999 | Valint, Jr. et al. .......... 526/279 |
| 6,008,317 A | 12/1999 | Lai et al. .................... 528/374 |
| 6,037,328 A | 3/2000 | Hu et al. ..................... 514/23 |
| 6,071,439 A | 6/2000 | Bawa et al. ................ 264/1.1 |

Primary Examiner—Charles Boyer
(74) Attorney, Agent, or Firm—John E. Thomas

(57) ABSTRACT

The invention provides a method for inhibiting the binding of a biguanide antimicrobial in aqueous solution to a hydrogel in contact with said solution comprising providing in said solution an amount of cyclodextrin sufficient to inhibit sorption of the biguanide antimicrobial to a hydrogel.

11 Claims, No Drawings

COMPOSITION AND METHOD FOR INHIBITING UPTAKE OF BIGUANIDE ANTIMICROBIALS BY HYDROGELS

CROSS-REFERENCE TO RELATED APPLICATIONS

This application is related by disclosure of similar subject matter to pending application Ser. No. 09/738,808, filed Dec. 15, 2000.

FIELD OF THE INVENTION

This invention relates generally to a composition and method for storing, preserving and dispensing solutions for cleaning and disinfecting contact lenses.

BACKGROUND

Biguanide antimicrobials such as alexidine and PHMB are widely used as antimicrobials in ophthalmic solutions, for example, contact lens cleaning, disinfecting and have been commercialized in various products, typically at levels of about 1 ppm or less for use with soft contact lenses. It is generally desirable to provide the lowest possible level of antimicrobial that is consistent with reliable disinfection in order to provide a generous margin for safety and comfort.

U.S. Pat. No. 4,758,595 to Ogunbiyi et al. discloses a contact-lens solution containing a polyaminopropyl biguanide (PAPB), also known as polyhexamethylene biguanide (PHMB) in combination with a borate buffer. These disinfecting and preservative solutions are especially noteworthy for their broad spectrum of bactericidal and fungicidal activity at low concentrations coupled with very low toxicity when used with soft-type contact lenses.

Some of the most popular products for disinfecting lenses are multipurpose solutions that can be used to clean, disinfect and wet contact lenses, followed by direct insertion (placement on the eye) without rinsing. Obviously, the ability to use a single solution for contact-lens care is an advantage. Such a solution, however, must be particularly gentle to the eye, since, as indicated above, some of the solution will be on the lens when inserted and will come into contact with the eye.

With conventional contact-lens cleaners or disinfectants, including multi-purpose solutions, lens wearers typically need to digitally or manually rub the contact lenses (typically between a finger and palm or between fingers) during treatment of the contact lenses. The necessity for the daily "rubbing" of contact lenses adds to the time and effort involved in the daily care of contact lenses. Many contact-lens wearers dislike having to perform such a regimen or consider it to be an inconvenience. Some wearers may be negligent in the proper "rubbing" regimen, which may result in contact-lens discomfort and other problems. Sometimes rubbing, if performed too rigorously, which is particularly apt to occur with beginning lens wearers, may damage the lenses. This can be problematic when a replacement lens is not immediately available.

Contact lens solutions that qualify as a "Chemical Disinfecting Solution" do not require rubbing to meet biocidal performance criteria (for destroying representative bacteria and fungi) set by the US Food and Drug Administration (FDA) under the Premarket Notification (510 k) Guidance Document For Contact Lens Care Products, May 1, 1997. In contrast, a contact-lens solution, referred to as a "Chemical Disinfecting System," that does not qualify as a Chemical Disinfecting Solution, requires a rubbing regimen to pass biocidal performance criteria. Traditionally, multi-purpose solutions (used for disinfecting and wetting or for disinfecting, cleaning, and wetting) have qualified as a Chemical Disinfecting System, but not as a Chemical Disinfecting Solution.

A Chemical Disinfecting Solution would generally require a more efficacious or stronger disinfectant than a Chemical Disinfecting System. The stronger the biocidal effect of a solution, however, the more likely that it may exhibit toxic effects or adversely effect lens-wearer comfort. For example, many very efficacious bactericides used in other contexts, such as mouthwashes, cosmetics, or shampoos, while being sufficiently safe for use in such products, would be too toxic for ophthalmic use, especially for use with soft lenses because of the above-mentioned tendency of soft lenses to bind chemicals and the sensitivity of eye tissues. Similarly, the concentrations of certain bactericides may need to be within lower limits in solutions for use with soft contact lenses than in other products or in solutions for other types of lenses, especially when such solutions are not rinsed from the contact lens before placing the lens in the eye.

It would be desirable to obtain a contact-lens solution that would simultaneously provide both (1) an increased level and/or broader spectrum of biocidal activity, and (2) a low order of toxicity to eye tissue, such that the solution can be used to treat a contact lens such that the lens can subsequently be placed on the eye without rinsing the solution from the lens. While challenging to develop, it would be especially desirable to obtain a Chemical Disinfecting Solution that could be used for soft contact lenses and that would allow direct placement of a contact lens on an eye following soaking in the solution and/or rinsing and rewetting with the solution. Such a product may provide increased efficacy, resulting in greater protection to the lens wearer against infection caused by microorganisms, while providing maximum convenience. Finally, it would be desirable for the biocidal efficacy of the disinfecting solution to be sufficiently high to achieve the efficacious disinfection, or at least not inherently inefficacious disinfection, of a contact lens with respect to bacteria and fungi in the event, for whatever reason, that the contact lens wearer does not carry out a regimen involving mechanical rubbing or the like using the contact-lens solution.

SUMMARY OF THE INVENTION

The invention provides, in a first aspect, a method and composition for inhibiting the binding of a biguanide antimicrobial in aqueous solution to a hydrogel in contact with said solution comprising providing in said solution an amount of cyclodextrin sufficient to inhibit binding of the biguanide antimicrobial to the hydrogel. The composition of the invention may comprise additional components, for example, at least one selected from the group consisting of buffers, sequestering and/or chelating agents, tonicity adjusting agents, surfactants, pH adjusting agents and viscosity builders.

The invention also provides a method and composition for cleaning contact lenses is provided comprising contacting the lenses with a composition containing an effective amount of one or more biguanide antimicrobials and from 0.0001% to about 10% by weight of one or more cyclodextrins for a time sufficient to clean the lenses. In a preferred embodiment, the composition is a multipurpose contact lens solution for cleaning and disinfecting contact lenses, and contains other components such as including buffers, chelating and/or sequestering agents, tonicity adjusting agents, surfactants, pH adjusting agents and viscosity builders.

The invention still further provides a composition for rewetting, disinfecting and/or cleaning hydrogel contact lenses comprising at least one biguanide antimicrobial and an amount of cyclodextrin that is:

(a) insufficient of itself to effectively clean contact lenses if that amount of cyclodextrin were present in the solution in the absence of at least one other cleaning agent; and (b) at least sufficient to inhibit the sorption of a biguanide antimicrobial to the hydrogel contact lenses.

In a preferred embodiment, the composition comprises a biguanide antimicrobial selected from the group consisting of poly(hexamethylene)biganide and alexidine. The composition preferably comprises at least one buffer at least one chelating agent or sequestering agent. The composition may suitably comprise at least one tonicity-adjusting agent, as well as surfactants, pH adjusting agents and viscosity builders.

DESCRIPTION OF THE INVENTION

The composition of the present invention is, in one embodiment, an aqueous biguanide-containing solution disinfecting solution, for example, a multipurpose contact lens solution. The composition of the invention contains one or more cyclodextrins together with one or more biguanide antimicrobials in a suitable carrier. Other active or inactive components can also be employed in the compositions, including buffers, chelating and/or sequestering agents, tonicity adjusting agents, surfactants, pH adjusting agents and viscosity builders.

The cyclodextrins useful in the present invention are cyclic oligosaccharides that may be produced by the enzymatic degradation of starch and have multiple glucose or glucopyranose units, usually 6 to 8 units. Depending on the particular preparation reaction conditions employed, cyclodextrins generally contain six, seven or eight of such units, connected by alpha-(1,4)bonds. The six, seven or eight unit cyclodextrins are commonly known as alpha-, beta-, and gamma-cyclodextrins, respectively.

Cyclodextrins have the shape of truncated cones with primary and secondary hydroxyl groups located at opposite ends of the torus. The glucosyl-o-bridges point into the center of the molecule and the primary hydrogel groups project from one outer edge while the secondary hydroxyl groups project from the other edge. The result is a molecule with a relatively hydrophobic center and a hydrophilic outer surface. These shapes and hydrophilic/hydrophobic domains provide for inclusion or incorporation of guest molecules into the center of the molecule.

Cyclodextrins are well known and are commercially produced by the enzymatic degradation of starch. For example, beta-cyclodextrin is the major product of the reaction between the enzyme cyclodextrin transglycosylase and a starch solution pretreated with gamma-amylase.

As used herein, the term "cyclodextrins" includes all cyclodextrin derivatives, such as cyclodextrin carbonates, ethers, esters, and polyethers; polymers or copolymers of polymerized cyclodextrins, such as polymerized beta-cyclodextrins; and substituted cyclodextrins such as those with functional groups bonded to one or more of the hydroxyl groups. Suitable function groups include, but are not limited to, methyl, ethyl, hydroxyethyl, and hydroxypropyl and acetyl groups. The cyclodextrin derivatives can also include cyclodextrins with functional groups replacing one or more of the hydroxyl groups such as amino-cyclodextrin, iodo-cyclodextrin and cyclodextrin sulfate. Some of these functional groups may also contribute preserving or disinfecting properties.

The preferred cyclodextrins are the beta-cyclodextrins and most preferred are beta-cyclodextrin selected from beta-cyclodextrin, hydroxypropyl beta-cyclodextrin, methyl beta-cyclodextrin and hydroxyethyl beta-cyclodextrin when the cyclodextrin compositions are employed at elevated temperatures.

The present invention employs an effective amount of cyclodextrin to inhibit the sorption of the biguanide by hydrogels, especially hydrogels suitable for fabricating contact lenses. The term "effective amount of cyclodextrin" as used herein means an amount of cyclodextrin sufficient to inhibit the sorption of the biguanide antimicrobial present in solution to the hydrogel. The amount of cyclodextrin may also vary with the required contact time between the hydrogel and the solution. For example, if the solution is a multipurpose solution for cleaning and disinfecting hydrogel contact lenses, the amount of cyclodextrin present in the multipurpose solution is preferably at least sufficient to inhibit the sorption of the biguanide antimicrobial.

In addition to multipurpose solutions, the invention is useful with ophthalmic solutions generally, including moisturizing eye drops and rewetting solutions, merely to name two examples.

The biguanide disinfectant is suitably present in concentration of from about 0.5 to about 10 ppm, preferably from about 1 to about 4 ppm. The cyclodextrin is suitably present in concentration of from about 0.1 to about 1.0 weight percent, preferably from about 0.2 to about 0.4 weight percent.

Hydrogels comprise hydrated, crosslinked polymeric systems containing water in an equilibrium state. Conventional hydrogel lens materials include polymers containing monomers such as 2-hydroxyethyl methacrylate (HEMA), glyceryl methacrylate, N-vinylpyrrolidone (NVP) and dimethacrylamide.

Flexible ophthalmic lens materials useful in the present invention include silicone hydrogels as well as conventional hydrogels and low-water elastomeric materials. Examples of flexible ophthalmic lens materials useful in the present invention are taught in U.S. Pat. No. 5,908,906 to Künzler et al.; U.S. Pat. No. 5,714,557 to Küinzler et al.; U.S. Pat. No. 5,710,302 to Küinzler et al.; U.S. Pat. No. 5,708,094 to Lai et al.; U.S. Pat. No. 5,616,757 to Bambury et al.; U.S. Pat. No. 5,610,252 to Bambury et al.; U.S. Pat. No. 5,512, 205 to Lai; U.S. Pat. No. 5,449,729 to Lai; U.S. Pat. No. 5,387,662 to Künzler et al. and U.S. Pat. No. 5,310,779 to Lai; which patents are incorporated by reference as if set forth at length herein.

U.S. Pat. Nos. 6,037,328, 6,008,317, 5,981,675, 5,981, 669, 5,969,076, 5,945,465, 5,914,355, 5,858,937, 5,824,719 and 5,726,733 teach ophthalmic lens materials containing HEMA monomers.

U.S. Pat. Nos 6,071,439, 5,824,719, 5,726,733, 5,708, 094, 5,610,204, 5,298,533, 5,270,418, 5,236,969 and 5,006, 622 teach ophthalmic lens materials containing glyceryl methacrylate monomers.

U.S. Pat. Nos. 6,008,317, 5,969,076, 5,908,906, 5,824, 719, 5,726,733, 5,714,557, 5,710,302, 5,708,094, 5,648,515 and 5,639,908 teach ophthalmic lens materials containing NVP monomers.

U.S. Pat. Nos. 5,539,016, 5,512,205, 5,449,729, 5,387, 662, 5,321,108 and 5,310,779 teach ophthalmic lens materials containing dimethacrylamide monomers.

The preferred conventional hydrogel materials typically contain HEMA, NVP and TBE (4-t-butyl-2-hydroxycyclohexyl methacrylate). Polymacon™ materials, for example the Soflens 66™ brand contact lenses (commercially available from Bausch & Lomb Incorporated of Rochester, N.Y.) are examples of particularly preferred conventional hydrogel materials.

Silicone hydrogels generally have a water content greater than about five weight percent and more commonly between about ten to about eighty weight percent. Materials are usually prepared by polymerizing a mixture containing at least one silicone-containing monomer and at least one hydrophilic monomer. Either the silicone-containing monomer or the hydrophilic monomer may function as a crosslinking agent (a crosslinker being defined as a monomer having multiple polymerizable functionalities) or a separate crosslinker may be employed. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

A preferred silicone hydrogel material comprises (in the bulk monomer mixture that is copolymerized) 5 to 50 percent, preferably 10 to 25, by weight of one or more silicone macromonomers, 5 to 75 percent, preferably 30 to 60 percent, by weight of one or more polysiloxanylalkyl (meth)acrylic monomers, and 10 to 50 percent, preferably 20 to 40 percent, by weight of a hydrophilic monomer. In general, the silicone macromonomer is a poly(organosiloxane)capped with an unsaturated group at two or more ends of the molecule. In addition to the end groups in the above structural formulas, U.S. Pat. No. 4,153,641 to Deichert et al. discloses additional unsaturated groups, including acryloxy or methacryloxy. Fumarate-containing materials such as those taught in U.S. Pat. No. 5,512,205; 5,449,729; and 5,310,779 to Lai are also useful substrates in accordance with the invention. Preferably, the silane macromonomer is a silicon-containing vinyl carbonate or vinyl carbamate or a polyurethane-polysiloxane having one or more hard-soft-hard blocks and end-capped with a hydrophilic monomer.

Suitable hydrophilic monomers include those monomers that, once polymerized, can form a complex with poly(acrylic acid). The suitable monomers form hydrogels useful in the present invention and include, for example, monomers that form complexes with poly(acrylic acid) and its derivatives. Examples of useful monomers include amides such as N,N-dimethyl acrylamide, N,N-dimethyl methacrylamide, cyclic lactams such as N-vinyl-2-pyrrolidone and poly(alkene glycol)s functionalized with polymerizable groups. Examples of useful functionalized poly(alkene glycol)s include poly(diethylene glycol)s of varying chain length containing monomethacrylate or dimethacrylate end caps. In a preferred embodiment, the poly(alkene glycol)polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. In a particularly preferred embodiment, the hydrophilic monomers used in the contact lens material are capable of forming a stable complex with a cationic polysaccharide.

Rigid ophthalmic lens materials include rigid-gas-permeable ("RGP") materials. RGP materials typically comprise a hydrophobic crosslinked polymer system containing less than 5 wt. % water. RGP materials useful in accordance with the present invention include those materials taught in U.S. Pat. No. 4,826,936 to Ellis; U.S. Pat. No. 4,463,149 to Ellis; U.S. Pat. No. 4,604,479 to Ellis; U.S. Pat. No. 4,686,267 to Ellis et al.; U.S. Pat. No. 4,826,936 to Ellis; U.S. Pat. No. 4,996,275 to Ellis et al.; U.S. Pat. No. 5,032,658 to Baron et al.; U.S. Pat. No. 5,070,215 to Bambury et al.; U.S. Pat. No. 5,177,165 to Valint et al.; U.S. Pat. No. 5,177,168 to Baron et al.; U.S. Pat. No. 5,219,965 to Valint et al.; U.S. Pat. No. 5,336,797 to McGee and Valint; U.S. Pat. No. 5,358,995 to Lai et al.; U.S. Pat. No. 5,364,918 to Valint et al.; U.S. Pat. No. 5,610,252 to Bambury et al.; U.S. Pat. No. 5,708,094 to Lai et al; and U.S. Pat. No. 5,981,669 to Valint et al. U.S. Pat. No. 5,346,976 to Ellis et al. teaches a preferred method of making an RGP material. The patents mentioned above are incorporated by reference as if set forth at length herein.

The cyclodextrin concentrations useful herein may be adjusted by one of ordinary skill in the art depending upon the desired contact time between the biguanide-containing solution and the poly(ethylene).

The cyclodextrin composition may contain a preserving or disinfecting amount of one or more antimicrobial agents in addition to the biguanide antimicrobial. The subject solution preferably includes at least one antimicrobial agent. As used herein, antimicrobial agents are defined as non-oxidative organic chemicals that derive their antimicrobial activity through a chemical or physiochemical interaction with the microbial organisms. Preferred antimicrobials are the quaternary ammonium compounds and biguanides.

Representative examples of the quaternary ammonium compounds are compositions comprised of benzalkonium halides or, for example, balanced mixtures of n-alkyl dimethyl benzyl ammonium chlorides. Other examples include polymeric quaternary ammonium salts used in ophthalmic applications such as poly[(dimethyliminio)-2-butene-1,4-diylchloride], [4-tris(2-hydroxyethyl)ammonio]-2-butenyl-w-[tris(2-hydroxyethyl)ammonio]dichloride (chemical registry number 75345-27-6) generally available as Polyquaternium 1® from ONYX Corporation.

Representative biguanides are the bis(biguanides), such as alexidine or chlorhexidine or salts thereof, and polymeric biguanides such as polymeric hexamethylene biguanides (PHMB).

Polymeric hexamethylene biguanides (commercially available from Zeneca, Wilmington, Del.), their polymers and water-soluble salts being most preferred. Generally, the hexamethylene biguanide polymers, also referred to as polyaminopropyl biguanide (PAPB), have molecular weights of up to about 100,000. Such compounds are known and are disclosed in U.S. Pat. No. 4,758,595 which patent is incorporated herein be reference.

A disinfecting amount of antimicrobial agent is an amount that will at least partially reduce the microorganism population in the formulations employed. Preferably, a disinfecting amount is that which will reduce the microbial burden by two log orders in four hours and more preferably by one log order in one hour. Most preferably, a disinfecting amount is an amount which will eliminate the microbial burden on a contact lens when used in regimen for the recommended soaking time (FDA Chemical Disinfection Efficacy Test— July, 1985 Contact Lens Solution Draft Guidelines). Typically, such agents are present in concentrations ranging from about 0.00001 to about 0.5% (w/v), and more preferably, from about 0.00003 to about 0.5% (w/v).

A second disinfectant/germicide can be employed as a solution preservative, but it may also function to potentiate, compliment or broaden the spectrum of microbiocidal activity of another germicide. This includes microbiocidally effective amounts of germicides which are compatible with and do not precipitate in the solution, in concentrations ranging from about 0.00001 to about 0.5 weight percent, and more preferably, from about 0.0001 to about 0.1 weight percent. Suitable complementary germicidal agents include, but are not limited to thimerosal or other phenylmercuric salts, sorbic acid, alkyl triethanolamines, and mixtures thereof.

The acid-addition salts of the germicides used in the present composition may be derived from an inorganic or organic acid. In most circumstances it is preferable that the salts be derived from an acid which is readily water-soluble and which affords an anion which is suitable for human usage, for example a pharmaceutically acceptable anion. Examples of such acids are hydrochloric, hydrobromic, phosphoric, sulphuric, acetic, D-gluconic, 2-pyrrolidino-5-carboxylic, methanesulphonic, carbonic, lactic and glutamic acids. The hydrochloride salt is preferred.

In the present application, the amount of the germicide or other components in a solution according to the present invention refers to the amount formulated and introduced into the solution at the time the solution is made.

Suitable chemical antimicrobial agents, as the term is used herein, include quaternary ammonium salts and polymers used in ophthalmic applications such as poly [(dimethyliminio)-2-butene-1,4-diyl chloride], [4-tris(2-hydroxyethyl)ammonio]-2-butenyl-W-[tris(2-hydroxyethyl) ammonio]dichloride (chemical registry number 75345-27-6), commercially available from ONYX Corporation; halides; trialkylammonium halides; biguanides such as salts of alexidine, alexidine free base, salts of chlorhexidine, hexamethylene biguanides and their polymers; and the like. The salts of alexidine and chlorhexidine can be either organic or inorganic and are typically gluconates, nitrates, acetates, phosphates, sulfates, halides and the like.

Suitable oxidative antimicrobial agents, as the term is used herein, include any peroxide sources which produce active oxygen in solution and any iodine liberating sources which produce preserving or disinfecting amounts of iodine compounds in solution. Examples of such agents include hydrogen peroxide and its alkali metal salts; alkali metal perborates and persulfates; alkali metal carbonate peroxide; diperisophthalic acid; peroxydiphosphate salts; sodium aluminium aminohydroperoxide; iodine and iodophors. Preferred oxidative antimicrobial agents are peroxides and iodophors. The antimicrobial agents can also be employed after the cleaning step using the cyclodextrin composition. In this application, the cleaning step would be followed with a disinfecting step in a conventional regimen.

A preserving amount of an antimicrobial agent is an amount that will substantially inhibit the microorganism population from growing while a disinfecting amount is an amount that will reduce the microorganism population. Preferably, a preserving amount of antimicrobial agent will substantially inhibit the microorganism population growth for at least thirty (30) days after exposure to environmental air. Preferably, a disinfecting amount of an antimicrobial agent is that which will reduce the microbial burden by about two log orders in four hours and, more preferably, by about one log order in one hour. Typically, such agents are present in concentrations ranging from about 0.00001% to about 0.5% (w/v), and more preferably, from about 0.00003% to about 0.05% (w/v).

The pH of the present solutions should be maintained within the range of 5.0 to 8.0, more preferably about 6.0 to 8.0, most preferably about 6.5 to 7.8, suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred, particularly for enhancing the efficacy of biguanides.

Generally, buffers will be used in amounts ranging from about 0.05 to 2.5 percent by weight, and preferably, from 0.1 to 1.5 percent. The disinfecting/preserving solutions of this invention preferably contain a borate or mixed phosphate buffer, containing one or more of boric acid, sodium borate, potassium tetraborate, potassium metaborate or mixtures of the same. In one embodiment, the solution of the invention may include a buffering system having a buffering capacity up to 40 ml of 0.01N HCl to change pH from pH 7.4 to 6.4 and up to 25 ml of 0.01 N NaOH to change pH from pH 7.4 to 8.4 and comprising 0.05~2.5% by weight of phosphate salt and 0.1~5.0% by weight of boric acid. The composition optionally further comprises an alkali or alkaline earth metal carbonates including sodium bicarbonate, sodium carbonate, potassium carbonate, potassium bicarbonate, and sodium bicarbonate. The most preferred carbonate is sodium carbonate.

If a carbonate buffer is used, it is suitably present in the amount of a buffering system having a buffering capacity up to 40 ml of 0.01 NHCl to change pH from pH 7.4 to 6.4 and up to 25 ml of 0.01~NaOH to change pH from pH 7.4 to 8.4 and comprising 0.05~2.5% by weight of phosphate salt and 0.1~5.0% by weight of boric acid.

The composition of the present invention may optionally includes a phosphonic acid, or its physiologically compatible salt, that is represented by the following Formula (I):

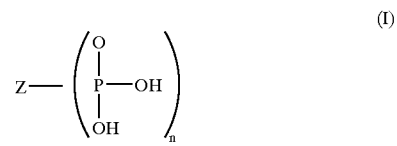
(I)

wherein Z is a connecting radical equal in valence to n, wherein n is an integer from 1 to 6, preferably 1 to 3.

If the solution contains a phosphonic acid buffer, the phosphonic acid buffer is suitably present in a concentration of at least 0.003 percent weight by volume of the subject phosphonic compound in the total solution, preferably 0.005 to 2.5 percent weight by volume and more preferably about 0.01 to 0.5 percent weight by volume in the total solution.

In a preferred embodiment, the solution comprises both a phosphate buffer and a borate buffer.

In addition to buffering agents, in some instances it may be desirable to include chelating and/or sequestering agents in the present solutions in order to bind metal ions which might otherwise react with the lens and/or protein deposits and collect on the lens. Dequest 2016 and its salts (disodium) are preferred examples. They are usually added in amounts ranging from about 0.01 to about 0.3 weight percent. Other suitable sequestering agents include gluconic acid, citric acid, tartaric acid (EDTA) and their salts, e.g. sodium salts.

Typically, the aqueous solutions of the present invention for treating contact lenses are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution that will cause stinging and eye irritation.

Examples of suitable tonicity adjusting agents include, but are not limited to: sodium and potassium chloride, dextrose, glycerin, calcium and magnesium chloride. These agents are typically used individually in amounts ranging from about 0.01 to 2.5% (w/v) and preferably, form about 0.2 to about 1.5% (w/v). Preferably, the tonicity agent will be employed in an amount to provide a final osmotic value of 200 to 450 mOsm/kg and more preferably between about 250 to about 350 mOsm/kg, and most preferably between about 280 to about 320 mOsm/Kg.

The present solution comprises at least one surfactant. Suitable surfactants can be either amphoteric, cationic, anionic, or nonionic which may be present (individually or in combination) in amounts up to 15 percent, preferably up to 5 percent weight by volume (w/v) of the total composition (solution). Preferred surfactants are amphoteric or nonionic surfactants; which when used impart cleaning and conditioning properties. The surfactant should be soluble in the eye care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available under the trademark Tween® 20), polyoxyethylene (23) lauryl ether (Brij® 35), polyoxyethyene (40) stearate (Myrj® 52), polyoxyethylene (25) propylene glycol stearate (Atlas® G 2612). One non-ionic surfactant in particular consisting of a poly(oxypropylene)-poly (oxyethylene) adduct of ethylene diamine having a molecular weight from about 7,500 to about 27,000 wherein at least 40 weight percent of said adduct is poly(oxyethylene) has been found to be particularly advantageous for use in cleaning and conditioning both soft and hard contact lenses when used in amounts from about 0.01 to about 15 weight percent. The CTFA Cosmetic Ingredient Dictionary's adopted name for this group of surfactants is poloxamine. Such surfactants are available from BASF Wyandotte Corp., Wyandotte, Mich., under the registered trademark "Tetronic". An analogous of series of surfactants, suitable for use in the present invention, is the poloxamer series which is a poly(oxyethylene) poly(oxypropylene) block polymers available under the trademark "Pluronic" (commercially available form BASF).

Various other ionic as well as amphoteric and anionic surfactants suitable for in the invention can be readily ascertained, in view of the foregoing description, from *McCutcheon's Detergents and Emulsifiers*, North American Edition, McCutcheon Division, MC Publishing Co., Glen Rock, N.J. 07452 and the *CTFA International Cosmetic Ingredient Handbook*, Published by The Cosmetic, Toiletry, and Fragrance Association, Washington, D.C.

Amphoteric surfactants suitable for use in a composition according to the present invention include materials of the type are offered commercially under the trade name "Miranol." Another useful class of amphoteric surfactants is exemplified by cocoamidopropyl betaine, commercially available from various sources.

The foregoing surfactants will generally be present in a total amount from 0.01 to 5.0 percent weight by volume (w/v), preferably 0.1 to 5.0 percent, and most preferably 0.1 to 1.5 percent.

It may also be desirable to include water-soluble viscosity builders in the solutions of the present invention. Because of their demulcent effect, viscosity builders have a tendency to enhance the lens wearer's comfort by means of a film on the lens surface cushioning impact against the eye. Included among the water-soluble viscosity builders are the cellulose polymers like hydroxyethyl or hydroxypropyl cellulose, carboxymethyl cellulose and the like. Such viscosity builders may be employed in amounts ranging from about 0.01 to about 4.0 weight percent or less. The present solutions may also include optional demulcents.

In a first embodiment of a method according to the present invention, the method comprises cleaning a contact lens with an aqueous solution comprising 0.005 to 1.0 percent by weight of at least one phosphonic acid compound, or its physiologically compatible salt, having 1 to 12, preferably 1 to 10 carbon atoms. The carbon atoms may be in the form of a substituted or unsubstituted branched or unbranched aliphatic, cyclic aliphatic, or aromatic groups or combinations thereof. Exemplary phosphonic acid compounds are those according to Formula (I) above. Preferably the phosphonic acid compound has 1 or 2 phosphonic acid groups which may be in salt form.

Preferably, the present method comprises soaking (no rubbing) a lens in the solution for a total period of time that is within a range of 2 hours to overnight, prior to direct placement of the lens in the eye. By the term "direct placement" is herein meant that the solution is not diluted or rinsed off the lens with a different contact-lens solution prior to "insertion" or placement on the eye.

In yet another embodiment of a method according to the present invention, the claimed solution may be used to clean a frequent replacement lens (FRL) that is planned for replacement after not more than about three months of use in the eye, or that is planned for replacement after not more than about 30 days of use in the eye, or that is planned for replacement after not more than about two weeks in the eye. Preferably, the lens is made from a polymer comprising about 0.0 to 5 mole percent repeat units derived from methacrylic acid (MAA), 10 to 99 mole percent of repeat units derived from hydroxyethyl methacrylate, and about 0.5 to 5 mole percent of cross-linking repeat units. Cross-linking repeat units may be derived, for example, from such monomers as ethyleneglycol dimethacrylate, divinylbenzene, and trimethylpropane trimethacrylate.

Separately from, or supplementally to, immersing a contact lens in a contact lens solution according to the present invention while the contact lens is outside the eye, the accumulation of proteins on hydrophilic contact lens can be further prevented by applying such a solution as eye drops. Thus, an opthalmologically safe solution comprising the claimed compound can be packaged in a container adapted for applying the solution as drops to the eye.

The hydroxypropyl methylcellulose (HPMC) functions to provide a desired level of viscosity and to provide demulcent activity. It is characterized as a mixed ether of cellulose containing a variable proportion of methoxyl and 2-hydroxypropoxyl groups and is purchased from Dow Chemical under the trademark Methocel E 15 LV -Premium. It is to be understood that the invention is not limited to any specific hydroxypropyl methylcellulose and that any equivalent HPMC of pharmaceutical grade may be used.

The ophthalmic solutions of this invention preferably contain a buffer system to control pH. Any pharmaceutically acceptable buffer system may be utilized. A preferred buffer system is provided by sodium borate/boric acid in amounts necessary to produce a pH of about 6.0 to 8.0. A preferred pH range is about 6.5–7.8 and a most preferred range is about 7.1–7.5.

The ophthalmic solutions of this invention are isotonic with respect to the fluids of the human eye. These solutions are characterized by osmolalities of 270–330 mOsm/kg. Osmolality of the solution of the invention is adjusted by means of sodium chloride and potassium chloride.

The solutions of the present invention may be formulated into specific contact lens care products, such as wetting solutions, soaking solutions, cleaning and conditioning solutions, as well as purpose type lens care solutions, etc. and mixtures thereof.

The solutions according to the present invention are physiologically compatible. Specifically, the solution must be "ophthalmically safe" for use with a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO standards and U.S. FDA (Food & Drug Administration) regulations. The solution should be sterile in that the absence of microbial contaminants in the product prior to release must be statistically demonstrated to the degree necessary for such products.

The present invention can be used with all contact lenses such as conventional hard, soft, rigid and soft gas permeable, and silicone (including both hydrogel and non-hydrogel) lenses, but is preferably employed with soft lenses. Such lenses are commonly prepared from monomers such as hydroxyethyl methacrylate, hydroxyethylmethyl methacrylate, vinylpyrrolidone, glycerolmethacrylate, methacrylic acid or acid esters and the like. Such lenses absorb significant amounts of water, which amounts range from about 4 to about 80 percent by weight. Preferably, the invention is formulated as a "multipurpose solution," meaning that the solution may be used for cleaning, chemical disinfection, storing, and rinsing a contact lens. Such solutions may be part of a "multipurpose solution system" or "multipurpose solution package." The procedure for using a multi-purpose solution, system or package is referred to as a "multi-functional disinfection regimen." Multi-purpose solutions do not exclude the possibility that some wearers, for example, wearers particularly sensitive to chemical disinfectants or other chemical agents, may prefer to rinse or wet a contact lens with another solution, for example, a sterile saline solution prior to insertion of the lens. The term "multipurpose solution" also does not exclude the possibility of periodic cleaners not used on a daily basis or supplemental cleaners for removing proteins, for example enzyme cleaners, which are typically used on a weekly basis. By the term "cleaning" is meant that the solution contains one or more cleaning agents in sufficient concentrations to loosen and remove loosely held lens deposits and other contaminants on the surface of a contact lens, especially if used in conjunction with digital manipulation (for example, manual rubbing of the lens with a solution) or with an accessory device that agitates the solution in contact with the lens, for example, a mechanical cleaning aid. The critical micelle concentration of a surfactant-containing solution is one way to evaluate its cleaning effectiveness.

A multipurpose solution preferably has a viscosity of less than 75 cps, preferably 1 to 50 cps, and most preferably 1 to 25 cps and is preferably is at least 95 percent weight by volume water in the total composition.

As stated, the multipurpose solution of the invention is useful for cleaning contact lenses. Although the multipurpose solution effectively cleans and disinfects by simply soaking a lens in the subject solution, the multipurpose solution cleans more effectively if a few drops of the solution are initially placed on each side of the lens, and the lens is rubbed for a period of time, for example, approximately 20 seconds. The lens can then be subsequently immersed within several milliliters of the subject solution. Preferably, the lens is permitted to soak in the solution for at least four hours. Furthermore, the lens is preferably rinsed with fresh solution after the rubbing step and again after being immersed within the solution. If the subject solution includes an antimicrobial agent, the subject solution not only cleans the lens, but also disinfects. However, it will be appreciated that other "non-chemical" disinfection means may be used, e.g. heat disinfection.

Although not generally necessary, enzymatic cleaners may also be used with the multipurpose contact lens solutions of the invention, especially for patients susceptible to high levels of protein deposition. If used, enzymatic tablets may be placed directly within the subject solution, is a manner like that described in U.S. Pat. No. 5,096,607.

EXAMPLES

The following examples evaluate whether the addition of cyclodextrin reduced the sorption of the biguanide Alexidine on SureVue® brand hydrogel contact lenses (commercially available from Johnson & Johnson Vision Care Incorporated of Jacksonville, Fla.).

TABLE 1

| Formulation | |
|---|---|
| Ingredients | % W/W |
| Sodium Chloride | 0.45% |
| Sodium Borate | 0.09% |
| Boric Acid | 0.85% |
| Alexidine HCl | 2–10 ppm |
| Beta-Cyclodextrin | 0.1–0.3% |
| Purified Water | Qs = 1000 ml |

Materials

Alexidine Solution (2–10 ppm)
Alexidine/0.1% β-Cyclodextrin Solution
Alexidine/0.3% β-Cyclodextrin Solution
15 SureVue ® Lenses
8 Standard Lens Cases Methods 1. Eighty-five gm of water was added into a beaker.
2. Sodium chloride, sodium borate, boric acid and beta-cyclodextrin were added and the mixture was stirred until each ingredient dissolved.
3. Then Alexidine HCl was added into the above mixture and mixed for more than five hours.
4. The final mixture was brought to 100 gm of total weight by adding purified water. The final solution has a pH of 7.0 and osmolality of 294 mOsm/kg.

5. 3-mL of each test solution, as well as the control solution, were placed into the lens cases for a total of 5 samples per solution.
6. SureVue® lenses were placed into each lens well aseptically.
7. Each lens was "dipped" into double-distilled water for approximately 2 seconds prior to installation into the lens cases.
8. Lenses were allowed to soak for approximately 18 hours (overnight).
9. 1-mL of solution from each of the lens wells was removed, analyzed and returned to the lens cases.

TABLE 2

Effect of Beta-Cyclodextrin on the uptake of Alexidine by SureVue ® Lenses

| Uptake of Alexidine By SureVue ® Lenses | Uptake of Alexidine by SureVue ® Lenses (0.1% Beta-Cyclodextrin) | Uptake of Alexidine by SureVue ® Lenses (0.3% Beta-Cyclodextrin) |
| --- | --- | --- |
| 75.26 ppm | 62.10 ppm 17.50% Inhibition | 31.04 ppm 58.75% Inbibition |

TABLE 3

ISO Stand Alone Microbiology Test

|  |  | Alexidine Solution | Alexidine Solution with Beta-Cyclodextrin |
| --- | --- | --- | --- |
| Fill Volume |  | 15 ml | 15 ml |
| Bottle Size |  | 15 ml | 15 ml |
| Test Disposition |  | Pass | Pass |
| Staphylococcus aureus | 10 minutes | >4.7 | 2.5 |
|  | 1 hour | >4.7 | 4.3 |
|  | 2 hours | >4.7 | >4.7 |
|  | 4 hours | >4.7 | >4.7 |
| Pseudomonas aeruginasa | 10 minutes | >4.6 | 3.6 |
|  | 1 hour | >4.6 | >4.6 |
|  | 2 hours | >4.6 | >4.6 |
|  | 4 hours | >4.6 | >4.6 |
| Serratia marcescens | 10 minutes | 2.3 | 3.6 |
|  | 1 hour | 4.6 | >4.6 |
|  | 2 hours | >4.6 | >4.6 |
|  | 4 hours | >4.6 | >4.6 |
| Candida albicans | 10 minutes | 2.8 | 1.4 |
|  | 1 hour | 3.5 | 3.0 |
|  | 2 hours | 4.6 | 4.3 |
|  | 4 hours | >4.6 | >4.6 |
|  | 24 Hours | >4.6 | >4.6 |
| Fusarium solani | 10 minutes | 2.9 | 3.0 |
|  | 1 hour | 3.8 | 3.7 |
|  | 2 hours | 3.7 | 4.1 |
|  | 4 hours | 4.0 | 4.1 |
|  | 24 hours | >4.1 | >4.1 |

What is claimed:

1. A method for inhibiting the binding of a biguanide antimicrobial in aqueous solution to a hydrogel in contact with said solution comprising providing in said solution an amount of cyclodextrin sufficient to inhibit binding of the biguanide antimicrobial to the hydrogel.

2. The method of claim 1 wherein the biguanide antimicrobial is selected from the group consisting of poly (hexamethylene) biganide and alexidine.

3. The method of claim 1 wherein said hydrogel is a silicone hydrogel.

4. The method of claim 1 wherein said solution further comprises at least one buffer.

5. The method of claim 1 wherein said solution further comprises at least one chelating agent or sequestering agent.

6. The method of claim 1 wherein said solution further comprises at least one tonicity adjusting agent.

7. The method of claim 1 wherein said solution further comprises at least one surfactant.

8. The method of claim 1 wherein said solution comprises at least one pH adjusting agent.

9. The method of claim 1 wherein said solution comprises at least one viscosity builder.

10. The method of claim 1 wherein said solution comprises from about 0.0001 to about 10 weight percent cyclodextrin.

11. The method of claim 10 wherein said solution comprises from about 0.01 to about 2.0 weight percent cyclodextrin.

* * * * *